(12) United States Patent
Thull

(10) Patent No.: US 9,603,972 B2
(45) Date of Patent: Mar. 28, 2017

(54) IMPLANT WITH ANTIMICROBIAL COATING

(75) Inventors: Roger Thull, Würzburg (DE); Ulrike Thull, legal representative, Basserdorf (CH)

(73) Assignee: Waldemar Link Gmbh & Co. KG (DE)

( * ) Notice: Subject to any disclaimer, the term of this patent is extended or adjusted under 35 U.S.C. 154(b) by 82 days.

(21) Appl. No.: 13/642,362

(22) PCT Filed: Apr. 13, 2011
(Under 37 CFR 1.47)

(86) PCT No.: PCT/EP2011/055808
§ 371 (c)(1),
(2), (4) Date: May 17, 2013

(87) PCT Pub. No.: WO2011/131536
PCT Pub. Date: Oct. 27, 2011

(65) Prior Publication Data
US 2013/0245783 A1    Sep. 19, 2013

(30) Foreign Application Priority Data
Apr. 19, 2010 (EP) ................................. 10004140

(51) Int. Cl.
A61F 2/28 (2006.01)
A61L 27/54 (2006.01)
A61L 31/16 (2006.01)

(52) U.S. Cl.
CPC ............... *A61L 27/54* (2013.01); *A61L 31/16* (2013.01); *A61L 2300/104* (2013.01); *A61L 2300/404* (2013.01)

(58) Field of Classification Search
CPC ......... A61L 2300/104; A61L 2300/404; A61L 31/16; A61L 27/54
(Continued)

(56) References Cited

U.S. PATENT DOCUMENTS 4,886,505 A    12/1989   Haynes et al.
5,295,979 A    3/1994    DeLaurentis et al.
(Continued)

FOREIGN PATENT DOCUMENTS

DE    102008008517    8/2009
GB    2073024    10/1981
(Continued)

OTHER PUBLICATIONS

Alicia M. Aguinaldo et al., Bacterial properties of silica particles with silver islands located on the surface, Jan. 19, 2007, Letters to the Editor/International Journal of Antimicrobial Agents, pp. 738-748.*

(Continued)

*Primary Examiner* — Brian Dukert
(74) *Attorney, Agent, or Firm* — McCarter & English, LLP

(57) ABSTRACT

The invention relates to an implant with a coating (23) which releases silver ions in the human body and as a result has antimicrobial action. According to the invention, a first surface component of the coating (23) is formed by an anode material (25). A second surface component of the coating (23) is formed by a cathode material (26). The cathode material is higher in the electrochemical voltage series than the anode material (25). The cathode material (26) and the anode material (25) are connected to one another in an electrically conductive manner. Together with the body electrolyte in the environment of the implant, the anode material (25) and the cathode material (26) form a multitude of local galvanic elements. The antimicrobial action of the coating (23) is improved as a result.

19 Claims, 5 Drawing Sheets

(58) Field of Classification Search
USPC .................................................. 623/23.57
See application file for complete search history.

(56) References Cited

U.S. PATENT DOCUMENTS

| | | | |
|---|---|---|---|
| 5,593,438 A * | 1/1997 | Akhavi | A61F 2/1613 |
| | | | 604/265 |
| 5,685,961 A | 11/1997 | Pourrezaei et al. | |
| 5,725,817 A * | 3/1998 | Milder | 264/104 |
| 6,287,484 B1 * | 9/2001 | Hausslein | A61F 2/30767 |
| | | | 252/512 |
| 6,663,634 B2 | 12/2003 | Ahrens et al. | |
| 2002/0029043 A1 | 3/2002 | Ahrens et al. | |
| 2006/0015053 A1* | 1/2006 | Crisp | 602/43 |
| 2010/0326835 A1 | 12/2010 | Speitling | |
| 2011/0272276 A1 | 11/2011 | Thull et al. | |

FOREIGN PATENT DOCUMENTS

| | | |
|---|---|---|
| JP | S57500588 A | 4/1982 |
| JP | H08506027 A | 7/1996 |
| RU | 2375942 C2 | 12/2009 |
| WO | WO 2009/100792 | 8/2009 |

OTHER PUBLICATIONS

PCT International Preliminary Report on Patentability and Written Opinion Issued on Oct. 23, 2012, with English translation, in connection with International Application No. PCT/EP2011/055808 (13 pages).

PCT International Search Report completed on Apr. 29, 2011, with English translation, in connection with International Application No. PCT/EP2011/055808 (5 pages).

Australian Patent Examination Report dated Dec. 6, 2013, issued in connection with Australian Patent Application No. 2011244526 (3 pages).

Office Action issued by the Korean Intellectual Property Office, along with its English translation, dated Feb. 7, 2014, issued in connection with Korean Patent Application No. 10-2012-7030288 (8 pages).

Examination Report issued by the Mexican Patent Office, along with its English translation, dated Oct. 28, 2015, issued in connection with Mexican Patent Application No. MX/a/2012/012125 (16 pages).

Office Action issued by Russian Intellectual Property Office, along with its English translation, dated Apr. 4, 2014, issued in connection with Russian Patent Application No. 2012148897/15 (6 pages).

Office Action issued by the Japanese Intellectual Property Office, along with its English translation, dated Apr. 15, 2014, issued in connection with Japanese Patent Application No. 2013-505404 (6 pages).

"Electrochemical Series", excerpted from CRC Handbook of Chemistry and Physics, 94th Edition, 2013, pp. 5-80 trhough 5-89 (11 pages).

European Search Report dated Aug. 31, 2010 in related European Application No. 10004140.9, available in German only (5 pages).

Office Action mailed Sep. 18, 2014, issued in connection with U.S. Appl. No. 13/088,844 (9 pages).

Office Action mailed Jun. 10, 2014, issued in connection with U.S. Appl. No. 13/088,844 (9 pages).

Office Action mailed Jan. 23, 2014, issued in connection with U.S. Appl. No. 13/088,844 (13 pages).

Office Action mailed Sep. 6, 2013, issued in connection with U.S. Appl. No. 13/088,844 (10 pages).

Office Action mailed Feb. 14, 2013, issued in connection with U.S. Appl. No. 13/088,844 (6 pages).

* cited by examiner

IMPLANT WITH ANTIMICROBIAL COATING

RELATED APPLICATIONS

This application is a U.S. National Phase Application under 35 U.S.C. 371 of International Application No. PCT/EP2011/055808 filed Apr. 13, 2011, which was published on Oct. 27, 2011 under International Publication Number WO 2011/131536 A1, which claims the benefit of European Patent Application No. 10004140.9 filed on Apr. 19, 2010. These applications are incorporated herein by reference in their entirety.

FIELD OF THE DISCLOSURE

The invention relates to an implant with a coating which releases silver ions in the human body and as a result has an antimicrobial effect.

BACKGROUND

When implants are introduced into the human body, there is a risk of infection. Triggers of infections can be microorganisms which are introduced into the human body with the implant or which are disposed on the surface of the implant. It is known that the risk of infection can be reduced by providing the implant with a coating that releases silver ions to its surrounding area. As is known, the silver ions have an antimicrobial effect. They furthermore have the advantage that—if they do not encounter a microorganism and exert an effect on this microorganism—they combine with the chloride of the body electrolyte to form AgCl and can be excreted from the body in this form. In contrast to other substances with an antimicrobial effect, the silver ions therefore do not accumulate in the body.

The known silver coatings only release silver ions to a limited extent. The released silver ions furthermore move at random in the vicinity of the implant. There is thus a high likelihood that the silver ions will combine in the body electrolyte to form AgCl and as a result will lose their antimicrobial effectiveness before they encounter a microorganism.

SUMMARY

The object forming the basis for the invention is to provide an implant, the coating of which has an improved anti-microbial effectiveness. Taking the prior art mentioned above as a starting point, the object is solved by the features of claim 1. Advantageous embodiments can be found in the sub-claims.

According to the invention, a first surface portion of the coating is formed by a silver-containing anode material, which is provided to release silver ions. A cathode material is provided for a second surface portion. The cathode material is situated higher in the electrochemical voltage series than the anode material. The cathode material and the anode material are connected to one another in an electrically conductive manner.

A few expressions will first of all be explained. The expression implant includes all types of objects that are to be inserted into the body. These are, for example, endo-prostheses for bones or joints, as well as implants that are introduced into other types of body tissue, such as, for example, stents in the cardiovascular system. Also included are implants that are only partially inserted into the human body and in part protrude therefrom, such as dental implants or external fixators that constitute an indirect, stabilising osteosynthesis external to the body which sometimes occurs with a tensioning device.

The expressions first surface portion and second surface portion express that the cathode material in the coating is spatially separated from the anode material. Not meant is thus a coating in which a plurality of materials are uniformly mixed with one another. It is possible, though not absolutely necessary, for the second surface portion to be extensively covered with the cathode material.

In the electrochemical voltage series, the substances are sorted in order of their standard electrode potential. The higher the position of a substance in the electrochemical voltage series, the lower its solution pressure, i.e. its tendency to release ions to water located in the surrounding area. A metal which is higher in the electrochemical voltage series is referred to as a precious metal; a metal which is lower in the electrochemical voltage series is referred to as a base metal. The position in the electrochemical voltage series is known for most substances, and the respective value can be taken from the relevant tables. If the position of a substance in the electrochemical voltage series is not known, it can be determined by forming a galvanic element with a known substance and measuring the resulting potential difference. The position in the voltage series can be determined based on the potential difference. The expressions anode material and cathode material serve to demonstrate the relative position of the used materials with respect to one another in the electrochemical voltage series. The anode material and the cathode material are electrically conductive materials.

When the implant is inserted into the body, the anode material and the cathode material of the coating form a local galvanic element with the body electrolyte located in the vicinity of the implant. The tendency of the anode material to release silver ions to the surrounding area is thereby increased. The electrons that remain in the anode material following the release of the silver ions can move into the cathode material as a result of the electrical connection. Owing to the potential difference, the silver ions are drawn in the direction of the cathode material.

The effect of the coating according to the invention is therefore twofold. Firstly, owing to the local galvanic element, the anode material has an increased tendency to release silver ions to the surrounding body electrolyte. Compared with a coating consisting solely of the respective anode material, a larger number of silver ions is thus released, as a result of which the antimicrobial effectiveness is increased. Furthermore, the movement of the released silver ions no longer occurs in random directions; rather, the silver ions are moved in the direction of the potential difference between the two substances, i.e. in the direction of the cathode material. The likelihood is increased that the silver ions will actually exert an effect on microorganisms disposed on the surface of the implant rather than combining in the body electrolyte to form AgCl and thereby losing the antimicrobial effectiveness. The effect of the coating according to the invention is therefore concentrated on the surface of the implant. The coating is particularly suitable for combatting the dangerous biofilm that can form on the surface of implants.

The coating may cover the entire surface of the implant. This would be suitable for many implants which are introduced into the body in their entirety. It may also be provided, in particular in the case of joint endoprostheses, that only part of the surface is coated. The coating may be applied to that part of the surface with which the prosthesis comes into contact with body tissue in the implanted state, whereas another part of the surface, which is intended, for example, to act together with another prosthesis component or which, as in the case of a fixator, is disposed outside of the body, is free of the coating.

The anode material may be pure silver. With a standard electrode potential of approximately +0.8 V, silver is a relatively precious metal which belongs in the upper range of the electrochemical voltage series. The normal hydrogen electrode is the reference parameter for the voltage values of the standard electrode potential.

The cathode material which acts together with the pure silver must have a standard electrode potential of more than +0.8 V. If the cathode material is a metal, it is therefore more precious than silver. A cathode material which is suitable for acting together with pure silver is, for example, gold, which has a standard electrode potential in the magnitude of +1.5 V. Even if pure silver is not used as the anode material, but rather an alloy of silver and another substance, the standard electrode potential of the cathode material should be greater than +0.8 V. The standard electrode potential of the cathode material is preferably at least 0.3 V, more preferably at least 0.5 V, more preferably at least 0.7 V higher than the standard electrode potential of the anode material.

The greater the difference between the standard electrode potential of the anode material and the standard electrode potential of the cathode material, the stronger the effect of the local galvanic element. In an advantageous embodiment, a silver-containing material is therefore used as the anode material, the standard electrode potential of which is lower than +0.8 V. The anode material then also contains other components in addition to the silver components that are supposed to dissolve out of the anode. The standard electrode potential specified for the anode material relates to the solution pressure for silver ions. Preferably selected as the anode is a material which releases no substances other than the silver ions to the body electrolyte. If other substances in addition to the silver ions are released, there is a risk that the other substances could have undesirable effects in the body. Furthermore, a material that is biocompatible should be selected for both the anode and the cathode.

The antimicrobial effect of the coating according to the invention depends on the silver ions that are released from the cathode material. The greater the surface portion of the coating occupied by the anode material, the higher the number of silver ions released. The surface portion of the coating that is occupied by the anode material is therefore preferably greater than 50%, more preferably greater than 70%, more preferably greater than 80%. In comparison, the surface portion occupied by the cathode material is of less importance. However, the portion of the cathode material may not be too small if a good effectiveness of the galvanic elements is to be achieved. The portion of the cathode material on the surface of the coating is preferably greater than 0.1%, more preferably greater than 1%, more preferably greater than 5%.

It is desirable for the silver ions, once they have left the anode material, to be able to travel a certain distance before encountering the cathode material. During this movement, the silver ions can exert an antimicrobial effect. The surface portions of the coating which are occupied by the anode material and the cathode material should therefore be separated from one another in such a manner that the silver ions do not necessarily immediately encounter the cathode material. The coating therefore preferably has a plurality of circular surface areas having a diameter of greater than 1 µm, more preferably of greater than 5 µm, more preferably of greater than 15 µm, more preferably of greater than 50 µm, which are formed solely of anode material and are free of cathode material. On the other hand, it is also not advantageous for the effectiveness of the coating if the free path over which the silver ions travel is too long. The diameter of the circular surface areas should therefore be smaller than 5 mm, preferably smaller than 1 mm, more preferably smaller than 0.5 mm. Preferably more than 30%, more preferably more than 50% of the surface of the coating is occupied by such surface portions.

Silver ions exiting in the centre of such an area have to travel a certain distance before they encounter cathode material. Whilst travelling this distance, they can exert an antimicrobial effect. The free path over which the silver ions are to travel can be guided by the diameter of the bacteria which is also in the µm range. It can be assumed that the silver ions move along an arc-shaped path and that the largest distance to the surface that the silver ions have on their path is of a similar order of magnitude to the distance traveled parallel to the surface. Thus, if the free path to be traveled corresponds approximately to the diameter of the bacteria, it is achieved that the silver ions can exert an effect on bacteria disposed on the surface along their entire path.

The coating may be designed such that the cathode material is embedded in the anode material in an island-shaped manner or is applied to the anode material in an island-shaped manner. The cathode material may even be applied in the form of connected surface areas having a diameter of, for example, a few µm. It is not out of the question that the cathode material is applied to the second surface area in the form of individual particles, without the anode material being extensively coated in this area.

In many cases, the surface of the implant is supposed to be smooth. This can be achieved if the anode material and the cathode material are flush against one another. In an alternative embodiment, cathode material may protrude relative to the anode material. The silver ions then move at a small distance to the surface of the coating, and thus a good effect on microorganisms in the immediate vicinity of the coating is achieved. It is suitable for this purpose to first of all apply the anode material with a uniform layer thickness and to then apply cathode material to the coating in selected regions. The layer thickness of the anode material may be between 100 nm and 10,000 nm, preferably between 200 nm and 400 nm. This range particularly applies if the anode material is pure silver. The layer thickness of the cathode material applied to the anode material may also be between 100 nm and 10,000 nm, preferably between 200 nm and 400 nm.

It is also possible to first of all extensively apply a layer of the cathode material. A layer of anode material can be applied to the cathode material, which comprises openings so that the cathode material can be accessed from the outside through the anode material. If the anode material is applied using a plasma coating method, the openings can be generated by aiming larger fragments having a diameter of, for example, 20 µm at the surface when applying the layer, which fragments remove a piece from the layer which is forming, cf. WO 2009/036846. When using this method, the thickness of the layers is also preferably between 100 nm and 10,000 nm, more preferably between 200 nm and 400 nm.

BRIEF DESCRIPTION OF THE DRAWINGS

The invention will be described in the following, by way of an example, by means of advantageous embodiments and with reference to the enclosed drawings.

DETAILED DESCRIPTION

Figure 1:
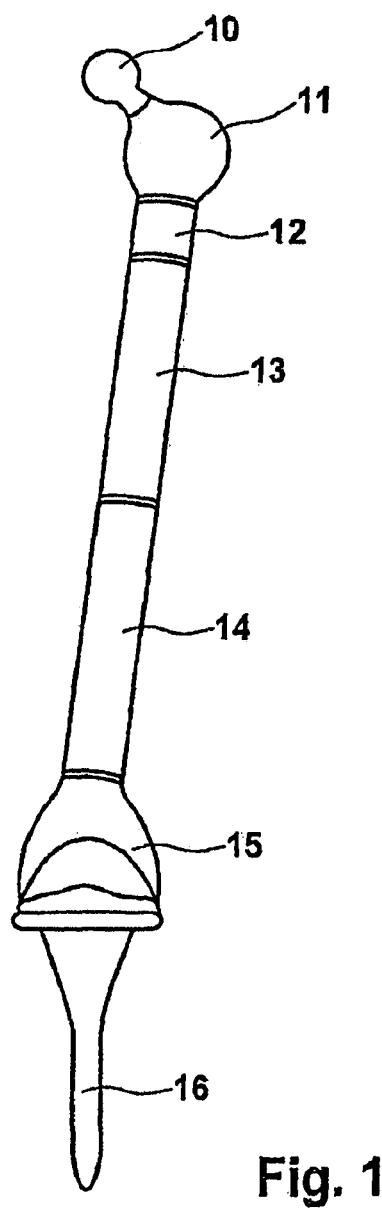
FIG. 1 shows a first embodiment of an implant according to the invention.

An implant shown in FIG. 1 is intended to replace a part of the human skeleton that extends from the hip to below the knee. A ball-shaped joint head 10 forms a joint surface that is designed to interact with an acetabulum. The joint head 10 is connected to a head piece 11 of the implant by means of a screw connection. The part of the implant which replaces the central shaft of the femur comprises three implant components 12, 13 and 14. The implant components 12, 13 and 14 are connected with one another and with the head piece 11 also by means of screw connections. A knee piece 15 forms an articulated connection to a shaft 16 that is intended to connect the implant to the tibia.

Figure 2:
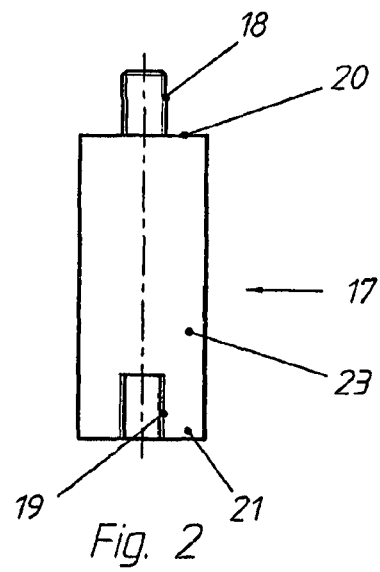
FIG. 2 shows a component of the implant of FIG. 1.

The implant components 12, 13 and 14 are available in different lengths so that the implant can be adapted to femurs of different lengths. FIG. 2 shows an enlarged view of an implant component 17 that corresponds to implant components 12, 13 and 14. Implant component 17 comprises a screw bolt 18 as well as a screw hole 19 that is indicated by dashed lines. By means of the screw bolt 18 and the screw hole 19, implant component 17 can be connected at both ends to further implant components. The screw bolt 18, the screw hole 19 and the adjoining end faces 20 and 21 therefore do not abut against body tissue of the patient in the implanted state of the implant component 17, but rather abut against other implant components. The outer surface 22 of the implant component 17 is, on the other hand, designed to come into contact with human tissue in the implanted state. The outer surface 22 is provided with an antimicrobial coating 23 that is indicated by dots. The remaining surface of the implant component is free of the coating 23.

Figure 4:
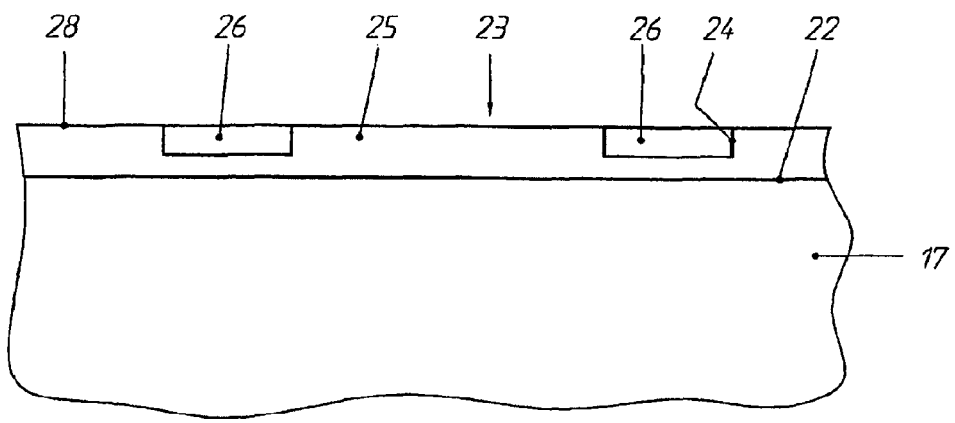
FIG. 4 shows a section of the body of an implant according to the invention which has a coating.
Figure 5:
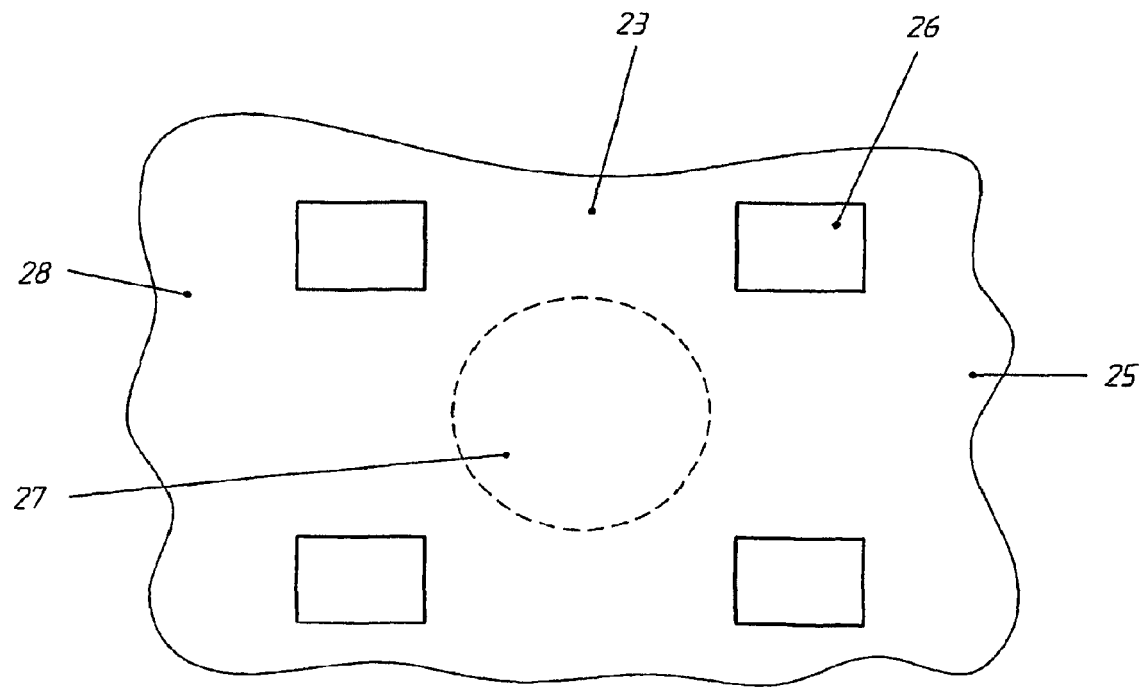
FIG. 5 shows the coating of FIG. 4 in a top view.

An enlarged view of the coating 23 is shown in FIGS. 4 and 5. The coating 23 consists for the most part of pure silver, which extensively covers the outer surface. As is shown in FIG. 5, gold material is introduced into the silver layer in the form of a plurality of rectangular islands. The gold material is embedded in the silver layer such that the two materials abut against one another in a flush manner and a smooth surface is formed. A smooth surface is desired since irritation of the surrounding body tissue owing to rubbing should be minimised. The coating 23 has a first surface portion 28, which is formed by the silver material, and a second surface portion 29, which is formed by the gold material. The surface portion 28, which is formed by the silver material, occupies more than 80% of the surface of the coating 23. As is indicated in FIG. 5 by means of a dashed line, circular surface areas 27 remain between the islands, in which the surface of the coating 23 consists entirely of silver material and is not interrupted by gold material. The surface area 27 has a diameter of more than 0.1 mm.

The silver and gold are connected to one another in an electrically conductive manner in the coating 23. Silver is a less precious metal than gold and is situated lower in the electrochemical voltage series than gold. Within the meaning of the function of the coating as according to the invention, silver is therefore an anode material 25 and gold is a cathode material 26.

Following implantation, the coating 23 is surrounded by body electrolyte. The silver material has a tendency to release positively charged silver ions to the body electrolyte. This tendency is referred to as solution pressure. When silver ions are released from the coating, excess electrons remain in the coating and an excess of negative charge carriers forms in the coating. Since the silver material and the gold material are connected to one another in an electrically conductive manner, the excess electrons can move freely in the direction of the gold material. The gold material is also subject to a certain solution pressure to release ions to the body electrolyte. Since gold is a more precious metal than silver and is situated higher in the electrochemical voltage series, the solution pressure is, however, lower than the solution pressure of silver. The silver ions that are released in a greater concentration move towards the gold material. In this manner, the body electrolyte, together with the silver as the anode material 25 and the gold as the cathode material 26, forms local galvanic elements. The silver ions leave the anode material 25 and move parallel to the coating 23 in the direction of the cathode material 26. In this manner, the silver ions can exert an antimicrobial effect on microorganisms that are disposed on the surface of the coating 23.

Figure 3:
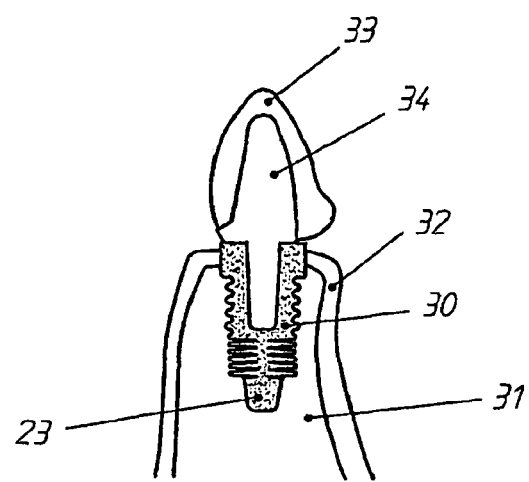
FIG. 3 shows a second embodiment of an implant according to the invention.

The dental implant shown in FIG. 3 is an alternative embodiment of the invention. An implant body 30 is screwed into the jawbone 31 at its lower end. The upper end of the implant body 30 protrudes upwardly from the jawbone 31 and the gum 32 surrounding the jawbone 31. A mounting post 34 that is covered with an artificial tooth crown 33 is screwed into the free end of the implant body 30. The dental implant replaces a natural tooth in this manner. The implant body 30 is in turn provided with a coating 23 that is indicated by means of dots.

Figure 6:
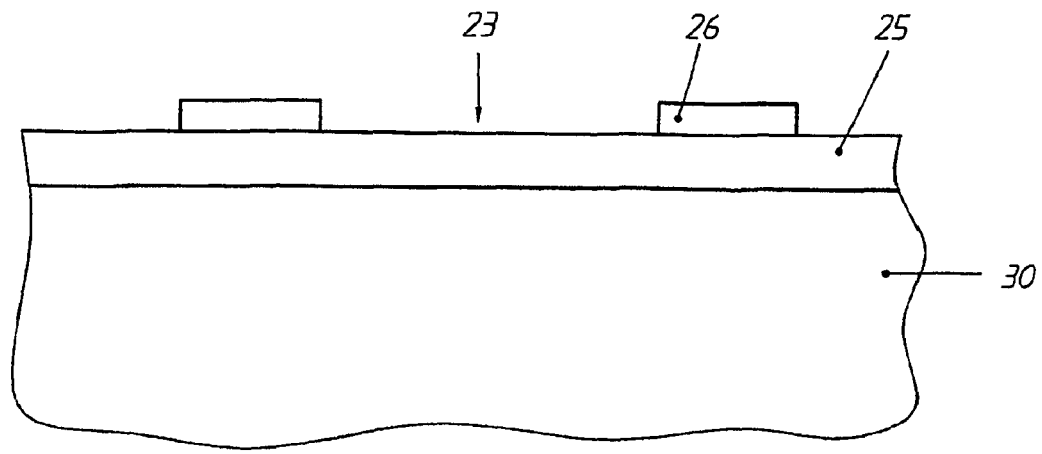
FIG. 6 shows the view of FIG. 4 in another embodiment of the invention.
Figure 7:
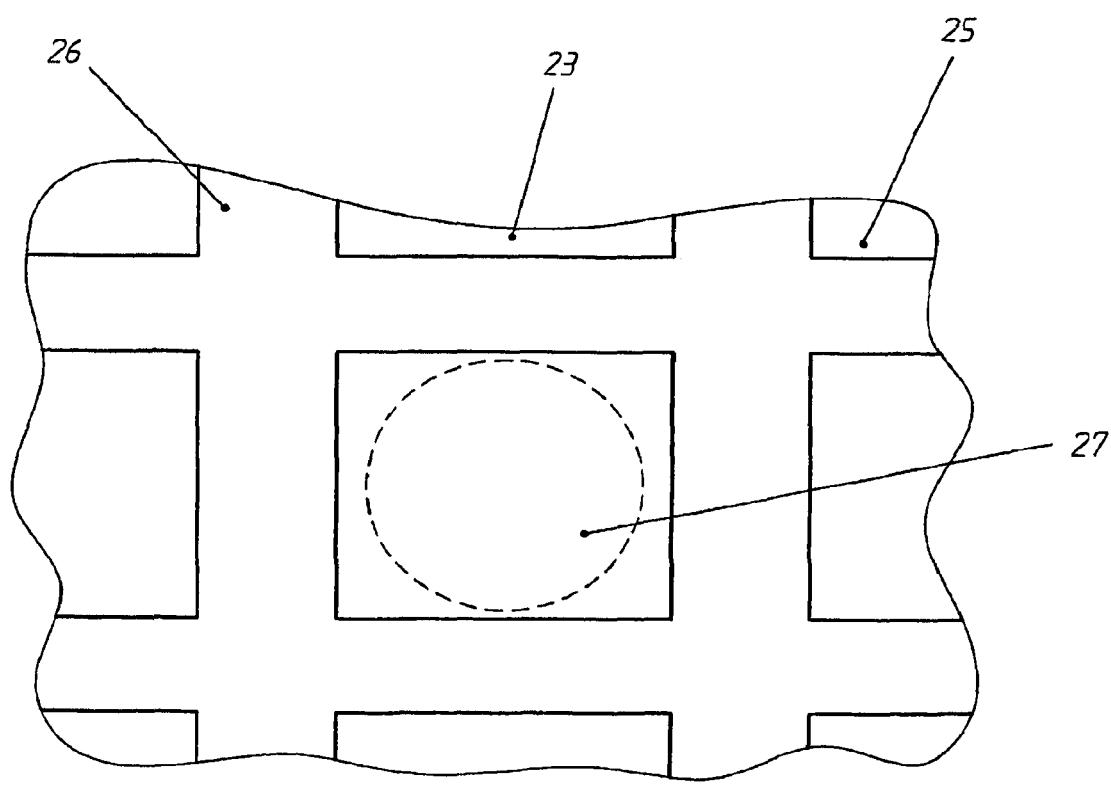
FIG. 7 shows the view of FIG. 5 in the embodiment according to FIG. 6.

The coating 23 is shown in an enlarged view in FIGS. 6 and 7. A silver coating is first of all applied to the surface of the implant 30, and has a uniform thickness of approximately 400 nm. Gold material is applied to the surface of the silver coating in a grid-like arrangement and also has a layer thickness of approximately 400 nm. The regions enclosed in the grid, in which the surface of the coating 23 is formed of the silver material, form, in their entirety, the first surface portion 28 of the coating 23. The grid-like arrangement of the gold material forms the second surface portion 29 of the coating. The grid shape of the gold material is dimensioned in such a manner that circular surface areas 27 having a diameter of more than 50 μm remain free of gold material.

Figure 8:
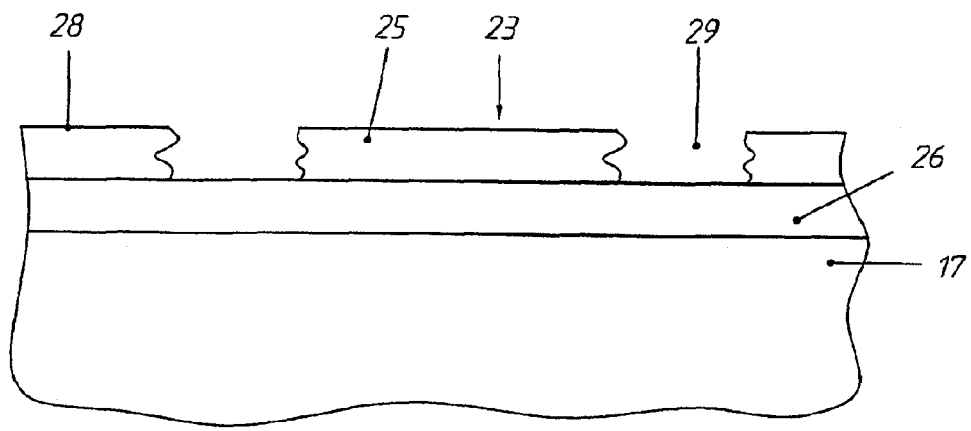
FIG. 8 shows the view of FIG. 4 in a further embodiment of the invention.

In the coating shown in FIG. 8, the implant component 17 is first of all extensively covered with a layer of gold as the cathode material 26. A silver layer applied thereto as the anode material 25 comprises a plurality of openings. The openings in their entirety form the second surface portion 29, in which the cathode material 26 can be accessed from the outside through the anode material 25.

Figure 9:
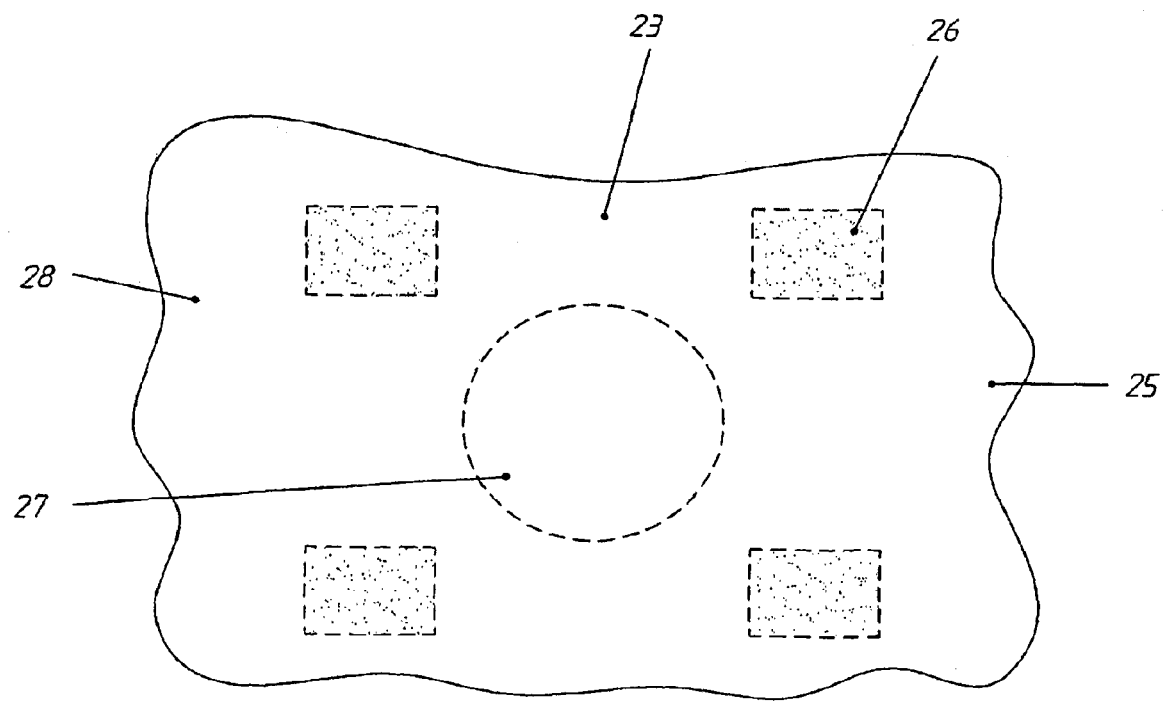
FIG. 9 shows the view of FIG. 5 in a further embodiment of the invention.

In the embodiment according to FIG. 9, the cathode material 26 is not extensively applied to the second surface portion 29, but is rather applied as a plurality of individual particles. This does not change anything about the effect of the coating as according to the invention.

As has already been explained above, the silver is an anode material 25 within the meaning of the invention and the gold is a cathode material 26. Together with the body electrolyte in the vicinity of the implant body 30, the coating 23 forms a plurality of local galvanic elements. Since the gold as the cathode material 26 protrudes relative to the anode material 25, the silver ions can also move at a slight distance to the silver layer in the direction of the cathode material 26.

In the case of the dental implant, the antimicrobial coating 23 has the particular function of exerting an effect on microorganisms at the transition between the implant body 30 and the gum 32 and/or the jawbone 31. It is well known that there are a number of microorganisms in the environment of the mouth and that the risk of an infection in the area surrounding the implant body 30 is high. If the antimicrobial coating 23 can prevent penetration of microorganisms between the implant body 30 and the gum 32, unpleasant infections for the patient can be avoided.

The invention claimed is:

1. An endoprosthesis for bones or joints having a coating which releases silver ions in the human body and as a result has an anti-microbial effect, comprising:
    a first surface portion of the coating formed by a silver-containing anode material;
    a cathode material provided on a second surface portion in the form of islands, said cathode material being situated higher in the electrochemical voltage series than the anode material;
    the cathode material and the anode material contacting each other and connected to one another in an electrically conductive manner; and
    the coating comprising a plurality of surface areas between the islands, the surface areas being formed entirely of anode material and free of cathode material, and the surface areas being larger than a circular area having a diameter of 1 micrometer.

2. The endoprosthesis for bones or joints according to claim 1, wherein the anode material is pure silver.

3. The endoprosthesis for bones or joints according to claim 1, wherein the standard electrode potential of the anode material, which is based on the release of silver ions, is less than +0.8 V.

4. The endoprosthesis for bones or joints according to claim 3, wherein the standard electrode potential of the cathode material is greater than +0.8 V.

5. The endoprosthesis for bones or joints according to claim 4, wherein the cathode material is gold.

6. The endoprosthesis for bones or joints according to claim 5, wherein the standard electrode potential of the cathode material is at least 0.3 V higher than the standard electrode potential of the anode material.

7. The endoprosthesis for bones or joints according to claim 1, wherein the cathode material is embedded in the anode material.

8. The endoprosthesis for bones or joints according to claim 7, wherein the first surface portion formed by the anode material occupies more than 50% of the surface of the coating.

9. The endoprosthesis for bones or joints according to claim 8, wherein the uncovered surface areas are smaller than a circular area having a diameter of 5 mm.

10. The endoprosthesis for bones or joints according to claim 9, wherein the anode material and the cathode material are flush against one another.

11. The endoprosthesis for bones or joints according to claim 1, wherein the cathode material protrudes relative to the anode material.

12. The endoprosthesis for bones or joints according to claim 1, wherein the cathode material is deposited on the anode material.

13. The endoprosthesis for bones or joints according to claim 5, wherein the standard electrode potential of the cathode material is at least 0.5 V higher than the standard electrode potential of the anode material.

14. The endoprosthesis for bones or joints according to claim 5, wherein the standard electrode potential of the cathode material is at least 0.7 V higher than the standard electrode potential of the anode material.

15. The endoprosthesis for bones or joints according to claim 7, wherein the first surface portion formed by the anode material occupies more than 70% of the surface of the coating.

16. The endoprosthesis for bones or joints according to claim 7, wherein the first surface portion formed by the anode material occupies more than 80% of the surface of the coating.

17. The endoprosthesis for bones or joints according to claim 8, wherein the uncovered surface areas are smaller than a circular area having a diameter of 0.5 mm.

18. The endoprosthesis for bones or joints according to claim 8, wherein the uncovered surface areas are smaller than a circular area having a diameter of 1 mm.

19. The endoprosthesis for bones or joints according to claim 1, wherein the cathode material is deposited in the form of individual particles.

* * * * *